(12) United States Patent
Peters et al.

(10) Patent No.: US 6,179,845 B1
(45) Date of Patent: Jan. 30, 2001

(54) OBSTETRICAL VACUUM EXTRACTOR

(76) Inventors: Scott W. Peters, 103 Belle Creek Dr., Oak Ridge, TN (US) 37830; Donald L. Peters, 4020 NE. Minnesota, Bartlesville, OK (US) 74006

( * ) Notice: Under 35 U.S.C. 154(b), the term of this patent shall be extended for 0 days.

(21) Appl. No.: 09/388,507

(22) Filed: Sep. 2, 1999

(51) Int. Cl.$^7$ ........................................ A61B 17/42
(52) U.S. Cl. .................. 606/123; 606/122; 606/119; 604/74
(58) Field of Search .................. 606/119, 121, 606/122, 123, 124–127; 604/74, 149, 902

(56) References Cited

U.S. PATENT DOCUMENTS

| 2,702,038 | 2/1955 | Uddenberg et al. |
| 3,202,152 | * 8/1965 | Wood et al. ............... 606/123 |
| 3,794,044 | 2/1974 | Vennard et al. |
| 4,512,347 | 4/1985 | Uddenberg. |
| 4,730,617 | 3/1988 | King. |
| 5,019,086 | * 5/1991 | Neward .................. 606/123 |
| 5,224,947 | * 7/1993 | Cooper et al. ............ 606/123 |
| 5,281,229 | * 1/1994 | Neward .................. 606/123 |
| 5,569,265 | 10/1996 | Elliott ..................... 606/123 |
| 5,693,058 | 12/1997 | Cavanagh et al. .......... 606/123 |
| 5,810,840 | * 9/1998 | Lindsay .................. 606/123 |
| 5,935,136 | * 8/1999 | Hulse et al. .............. 606/123 |

* cited by examiner

Primary Examiner—Pedro Philogene
(74) Attorney, Agent, or Firm—William R. Sharp

(57) ABSTRACT

An obstetrical vacuum extractor is disclosed herein which comprises: a vacuum cup having an interior; an elongated hollow stem having a longitudinal axis, a first open end fixedly joined to the cup so as to communicate with the cup interior, and an opposing second open end; and a handle having first and second handle portions on opposite sides of the stem longitudinal axis, the handle being mounted on the stem to allow rotation of the stem and cup with respect to the handle and substantially prevent axial movement of the handle on the stem.

13 Claims, 3 Drawing Sheets

OBSTETRICAL VACUUM EXTRACTOR

BACKGROUND OF THE INVENTION

The invention relates to an obstetrical vacuum extractor to assist in childbirth.

The conventional vacuum extractor has a vacuum cup at one end that is integral with a stem and handle. The stem is hollow so that a vacuum can be applied through the stem to the cup. Grasping the extractor with the handle, the physician places the cup on the head of the infant, and applies a partial vacuum through the hollow stem to the cup. A flexible edge at the mouth of the cup seals to the infant's head, and allows the physician to pull with the handle, transmitting this force to assist in delivery.

The above described vacuum extractor works well in pulling the infant out of the birth canal. However, the infant's head will sometimes rotate as it descends through the birth canal. The cup can rotate on the infant's head without breaking the seal, and injury can occur if the cup does not rotate in unison with the head. In such cases, the physician is required to manually rotate the handle at the same time as the head rotates. This can be a difficult procedure to accomplish.

SUMMARY OF THE INVENTION

The invention pertains to an obstetrical vacuum extractor comprising: a vacuum cup having an interior; an elongated hollow stem having a longitudinal axis, a first open end fixedly joined to the cup so as to communicate with the cup interior, and an opposing second open end; and a handle having first and second handle portions on opposite sides of the stem longitudinal axis, the handle being mounted on the stem to allow rotation of the stem and cup with respect to the handle and substantially prevent axial movement of the handle on the stem.

Accordingly, as the infant's head rotates in the manner discussed above, the physician can pull on but not rotate the handle as the stem and up rotate in unison with the infant's head, thereby decreasing the possibility of injury.

DETAILED DESCRIPTION OF THE INVENTION

Figure 1:
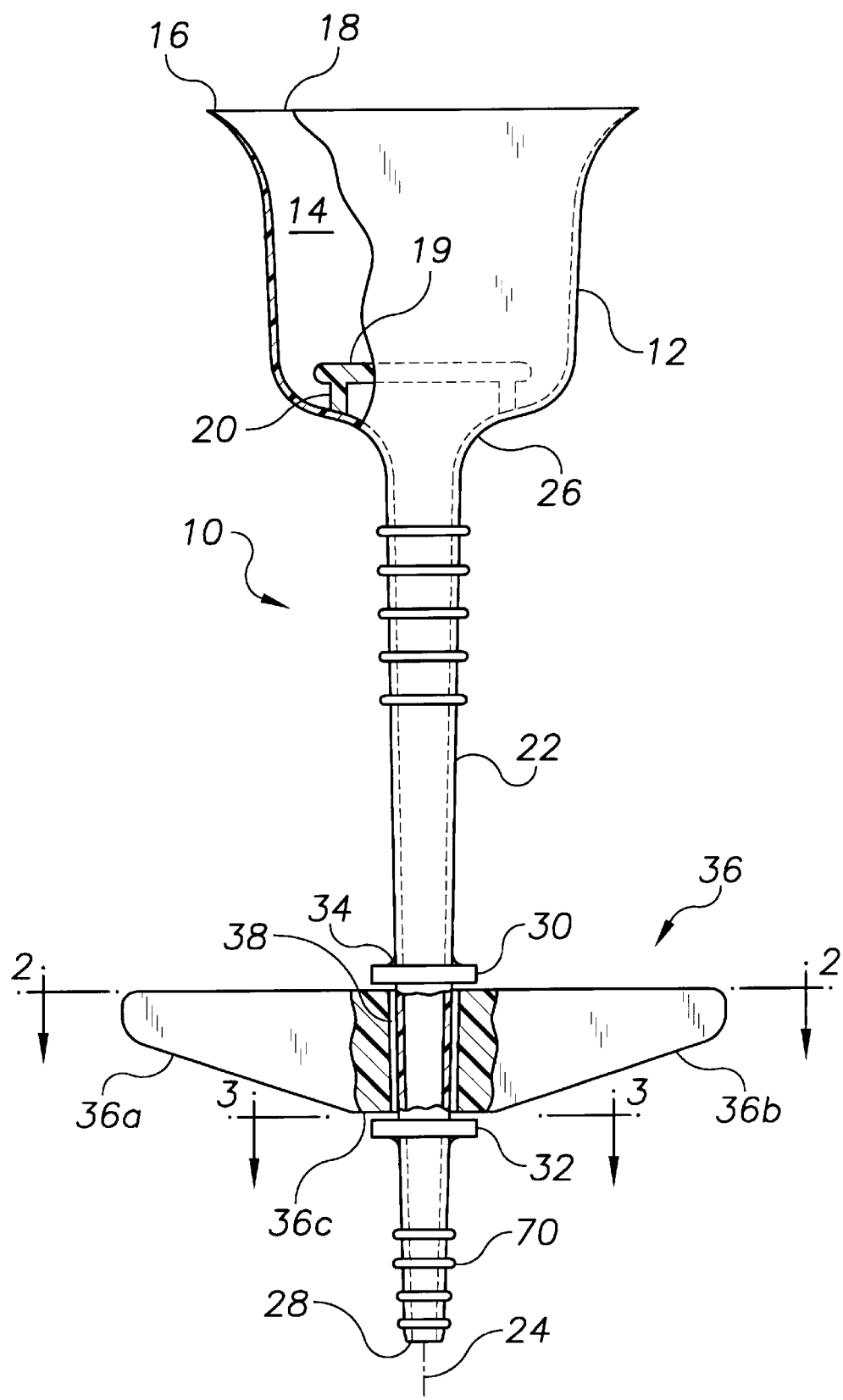
FIG. 1 is a side view of one embodiment of a vacuum extractor in acccordance with the invention, with certain portions of the extractor shown in cross section to more clearly show structural detail.

Referring to FIG. 1, vacuum extractor 10 includes a vacuum cup 12 having an interior 14. Cup 12 is preferably bell shaped with a wall that flares outwardly to an edge 16. Edge 16 defines a mouth 18. As shown, the wall of cup 12 becomes progressively thinner as it flares toward edge 16. Such wall at edge 16 is sufficiently flexible to make an effective seal upon the surface of an infant's head. A disc shaped vacuum distributor 19 is fixedly positioned within interior 14 by means of posts 20.

Vacuum extractor 10 further includes an elongated hollow stem 22 having a longitudinal axis 24, an open end 26 fixedly joined to and preferably integral with cup 12 so as to communicate with interior 14, and an opposing open end 28. A pair of longitudinally spaced bosses 30 and 32 transversely extend from and surround stem 22. In the embodiment of FIG. 1, bosses 30 and 32 are fixedly connected to stem 22, preferably by means of welds. A weld is indicated at 34. A handle 36 has handle portions 36a and 36b on opposite sides of longitudinal axis 24, and also has a central portion 36c (shown in cross section), positioned between bosses 30 and 32, with an opening 38 through which stem 22 extends.

In the embodiment of FIG. 1, handle 36 is of a unitary construction, comprising a single integral piece. Employing such a unitary construction is possible because the bosses can be sequentially welded (i.e. fusion or sonic) onto stem 22. For example, boss 30 can be welded to the desired location on stem 22, then handle 36 can be slipped over stem 22 to a position adjacent to boss 30. Boss 32 can then be welded to stem 22 at its proper location to complete assembly.

As shown, and at any location between the upper and lower ends of central portion 36c, opening 38 has a diameter slightly larger than the outside diameter of stem 22. Of course, opening 38 is also tapered to match the taper of stem 22. In addition, the longitudinal distance between the upper and lower ends of central portion 36c is slightly less than the longitudinal distance between the lower face of boss 30 and the upper face of boss 32.

It should be readily apparent from FIG. 1 and the above description that the manner in which handle 36 is mounted on stem 22, with its central portion between the bosses, allows rotation of stem 22 and cup 12 with respect to handle 36 and also substantially prevents axial movement of the handle on the stem. Bosses 30 and 32 essentially function as thrust bearings.

Figure 2:
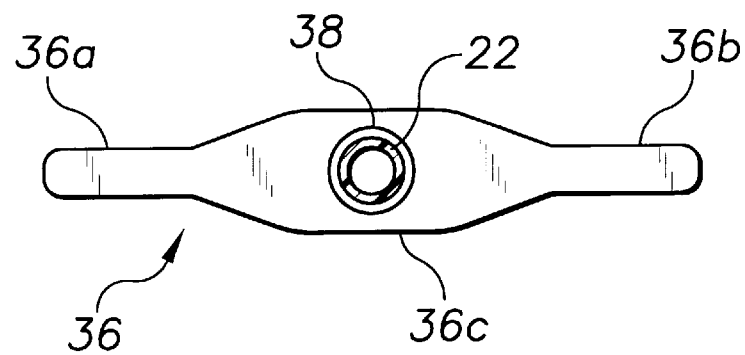
FIG. 2 is a view of the vacuum extractor as viewed along line 2—2 in FIG. 1.

Referring to FIG. 2, this view shows stem 22 in cross section within opening 38, and also shows the top of handle 36 with its handle portions 36a and 36b and its central portion 36c.

Figure 3:
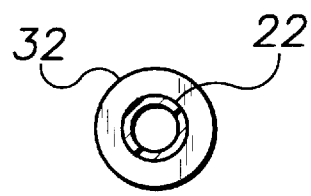
FIG. 3 is a view of the vacuum extractor as viewed along line 3—3 in FIG. 1.

Referring to FIG. 3, this view also shows stem 22 in cross section and also the preferred substantially annular shape of boss 32. Boss 30 has the same shape.

Figure 4:
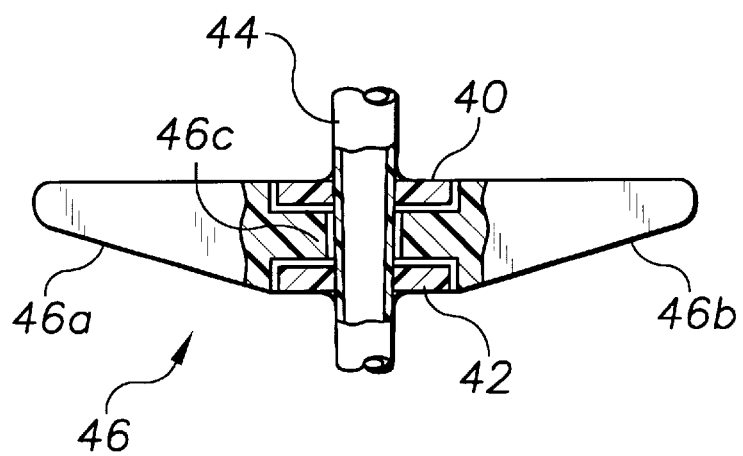
FIGS. 4 and 5 are fragmentary views illustrating other embodiments of the vacuum extractor, with certain portions shown in cross section.

Referring to FIG. 4, another embodiment is shown having a pair of bosses 40 and 42 (shown in cross section) welded to a stem 44, and also a handle 46 of a unitary construction with handle portions 46a and 46b. This embodiment differs from the embodiment of FIG. 1 insofar as central portion 46c (shown in cross section) comprises a substantially annular flange that fits between the bosses.

Figure 5:
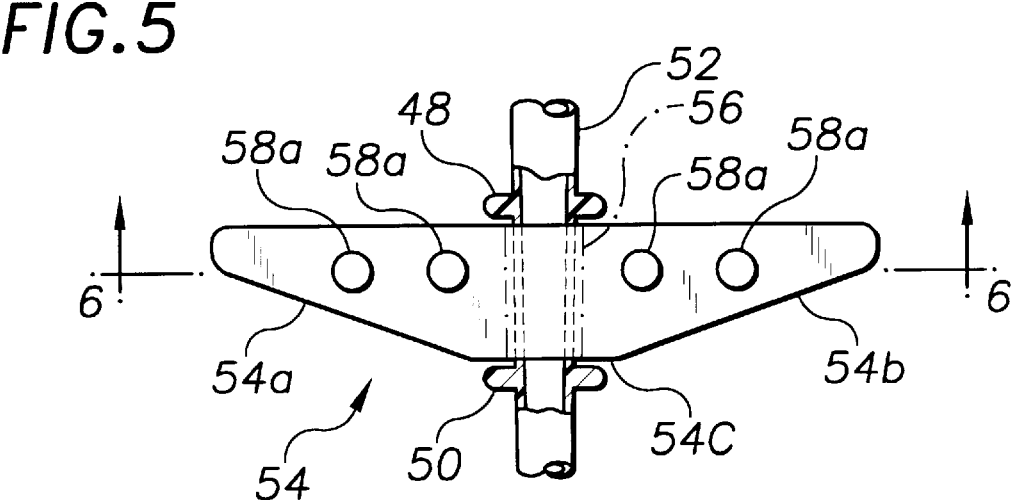

Referring to FIG. 5, another embodiment is shown in which bosses 48 and 50 (shown in cross section) are integral with stem 52. This can be easily accomplished when molding the stem. Handle 54 has handle portions 54a and 54b, as well as a central portion 54c with an opening 56 (indicated by a broken line alternating with dots) through which stem 52 extends (as indicated by broken lines). Handle 54 is of a split construction in order to mount the handle with its central portion 54c between bosses 48 and 50.

Figure 6:
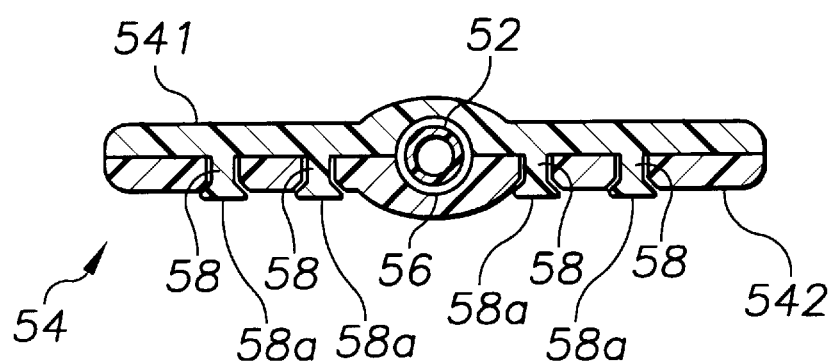
FIG. 6 is a cross-sectional view as viewed along line 6—6 in FIG. 5, illustrating a handle of a split construction.

This split construction of handle 54 is illustrated in the cross-sectional view of FIG. 6, which also shows stem 52 within opening 56. Handle 54 has a first half 541 joined to a second half 542. First half 541 has a plurality of posts 58 extending through corresponding holes of second half 542. Each post 58 has an enlarged end 58a that fits within an outer chamfered portion of the corresponding hole of second half 542 so as to retain the two halves together. The two halves can be mated together in this manner by starting with posts 58 that are longer than that shown and uniform in diameter, and then heating the exposed end of each post 58 with a hot mandrel to thereby form each enlarged end 58a. A side view of enlarged ends 58a is shown in FIG. 5.

Figure 7:
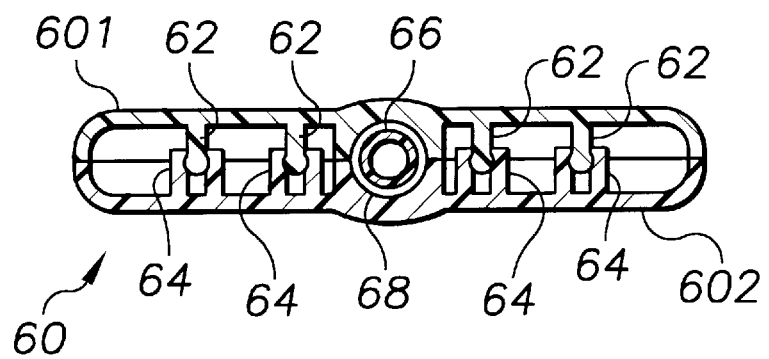
FIG. 7 is a cross-sectional view showing another embodiment of a split handle.

FIG. 7 shows another embodiment of a split handle that is substantially hollow, thus requiring generally less material for its formation. Handle 60 has a first half 601 joined to a second half 602. First half 601 has a plurality of posts 62 with enlarged ends, and second half 602 has a plurality of corresponding female receptacles 64 for receiving the enlarged ends therein so that the two halves are snap locked together. A stem 66 as received within a central portion opening 68 is also shown in FIG. 7.

With respect to materials of construction, the stem and vacuum cup can be comprised of any moldable plastic material as long as the wall of the stem is sufficiently thick to be relatively stiff and rigid and the wall of the cup at its edge is sufficiently thin to be somewhat flexible. In the embodiments of FIGS. 1–4, the bosses are preferably a substantially rigid plastic material that can be the same as or different than the plastic material employed for the stem and cup. Of course, in the embodiments of FIGS. 5–7, where the bosses are integral with the stem, the bosses, stem, and cup are all comprised of the same moldable plastic material. In each of the embodiments, the handle is also preferably a plastic material, most preferably a sturdy plastic such as high density polyethylene.

Referring back to FIG. 1, when in use, a tube (not shown) is slipped over open end 28 and circumferential ribs 70, which assist in maintaining an air-tight seal. The tube is connected to a suitable vacuum source (not shown). Edge 16 of vacuum cup 12 is applied to the top of the infant's head, and a vacuum is applied through stem 22 to cup 12 to effect a seal on the head. The physician then grasps handle portions 36a and 36b with one hand, and starts to gently pull to assist in delivery of the infant. If and when the infant's head starts to rotate, the physician can pull on but not rotate handle 36 while stem 22 and cup 12 rotate in unison with the infant's head, thereby decreasing the possibility of injury.

Obviously, many modifications and variations of the present invention are possible in light of the above teachings. For example, the central portion of the handle could have a longitudinally extending slot communicating with the central portion opening, allowing the stem between the bosses to be received through the slot and into the opening so as to snap the handle onto the stem. It is, therefore, to be understood that within the scope of the appended claims, the invention can be practiced otherwise than as specifically described.

That which is claimed is:

1. An obstetrical vacuum extractor comprising:
    a vacuum cup having an interior;
    an elongated hollow stem having a longitudinal axis, a first open end fixedly joined to the cup so as to communicate with the cup interior, and an opposing second open end; and
    a handle having first and second handle portions on opposite sides of the stem longitudinal axis, the handle being mounted on the stem to allow rotation of the stem and cup with respect to the handle and substantially prevent axial movement of the handle on the stem.

2. A vacuum extractor as recited in claim 1 further comprising a pair of longitudinally spaced bosses transversely extending from and surrounding the stem, wherein the handle has a central portion, positioned between the bosses, with an opening through which the stem extends so that the central portion is not affixed to the stem.

3. A vacuum extractor as recited in claim 2 wherein each boss is substantially annular in shape.

4. A vacuum extractor as recited in claim 2 wherein each boss is fixedly connected to the stem.

5. A vacuum extractor as recited in claim 4 wherein the handle is of a unitary construction.

6. A vacuum extractor as recited in claim 2 wherein each boss is integral with the stem.

7. A vacuum extractor as recited in claim 6 wherein the handle is of a split construction, having a first half joined to a second half.

8. A vacuum extractor as recited in claim 7 wherein one half has a plurality of posts extending through corresponding holes of the other half, the posts having enlarged ends to retain the two halves together.

9. A vacuum extractor as recited in claim 7 wherein one half has a plurality of posts with enlarged ends and wherein the other half has a plurality of corresponding female receptacles for receiving the enlarged ends therein so that the two halves are snap locked together.

10. A vacuum extractor as recited in claim 1 wherein the stem is joined to the vacuum cup so as to be integral therewith.

11. A vacuum extractor as recited in claim 10 wherein the stem and vacuum cup are comprised of a plastic, and the handle is comprised of a plastic.

12. An obstetrical vacuum extractor comprising:
    a vacuum cup having an interior;
    an elongated hollow stem having a longitudinal axis, a first open end fixedly joined to the cup so as to communicate with the cup interior, and an opposing second open end; and
    a handle having first and second handle portions on opposite sides of the stem longitudinal axis, the handle being rotatably mounted on the stem so as to allow rotation of the stem and cup with respect to the handle but substantially prevent axial movement of the handle on the stem.

13. An obstetrical vacuum extractor for use by a physician in delivery of an infant, comprising:
    a vacuum cup, having an interior, for being sealingly applied to the head of the infant;
    an elongated hollow stem having a longitudinal axis, a first open end fixedly joined to the cup so as to communicate with the cup interior, and an opposing second open end; and
    a handle having first and second handle portions on opposite sides of the stem longitudinal axis, the handle being mounted on the stem to allow rotation of the stem and cup with respect to the handle and substantially prevent axial movement of the handle on the stem, such that when the head of the infant rotates the physician can pull but not rotate the handle while the stem and cup rotate in unison with the infant's head.

* * * * *